United States Patent

Eschinasi et al.

[11] 4,294,767
[45] Oct. 13, 1981

[54] PROCESS FOR THE PREPARATION OF 2,5-DIMETHYL-4-HYDROXY-3(2H)-FURANONE AND ITS 2,5-DIALKYL HOMOLOGUES

[75] Inventors: Emile H. Eschinasi, Haifa, Israel; Enrico Castelli, Leumann, Italy

[73] Assignee: Instituto per la Ricerca Scientifica e Applicata di Technologie Alimentari S.p.A, Turin, Italy

[21] Appl. No.: 180,179

[22] Filed: Aug. 21, 1980

[51] Int. Cl.³ .......................................... C07D 307/32
[52] U.S. Cl. ................................................. 260/347.8
[58] Field of Search ..................................... 260/347.8

[56] References Cited
U.S. PATENT DOCUMENTS

| | | | |
|---|---|---|---|
| 3,651,097 | 3/1972 | van den Ouweland et al. | 260/347.8 |
| 4,127,592 | 11/1978 | Cohen | 260/347.8 |
| 4,181,666 | 1/1980 | Huber et al. | 260/347.8 |

*Primary Examiner*—Richard Raymond
*Attorney, Agent, or Firm*—Sughrue, Mion, Zinn, Macpeak & Seas

[57] ABSTRACT

2,5-dialkyl-4-hydroxy-3(2H)-furanones having the formula:

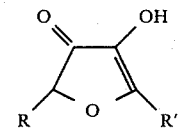

are obtained by the aldol condensation, under basic conditions, of a 2,5-dialkyl-dihydro-3(2H)-furanone with an aldehyde, R"CHO, and dehydration of the aldol to the corresponding exocyclic alkene:

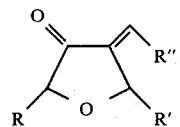

The alkene is then reacted with ozone in a participating solvent to give the hydroperoxy-hemiacetal which is reduced to the hemiacetal, this then being converted to the desired product by heating under reflux in acidic conditions in an inert atmosphere.

8 Claims, No Drawings

PROCESS FOR THE PREPARATION OF 2,5-DIMETHYL-4-HYDROXY-3(2H)-FURANONE AND ITS 2,5-DIALKYL HOMOLOGUES

BACKGROUND OF THE INVENTION

The present invention relates to the preparation of 2,5-dialkyl-4-hydroxy-3(2H)-furanones, and especially, but not exclusively, to the preparation of 2,5-dimethyl-4-hydroxy-3(2H)-furanone, commercially known under the trade name FURANEOL.

FURANEOL is an important aromatic substance found in pineapples (J. O. Rodin et al, J. Food Science (1965) 30, 280). It has a strong, fruity fragrance and is suitable for use in flavouring various food products (U.S. Pat. No. 3,887,589 of the Mar. 6, 1975) on account of its excellent aromatic and organoleptic properties.

According to J. E. Hodge and colleagues (U.S. Pat. No. 2,936,308), FURANEOL can be obtained in small quantities from rhamnose and piperidine acetate; however, rhamnose is very expensive and hence this process is uneconomic. Processes for synthesizing FURANEOL from other starting products are also known. The majority of these are based on the preliminary formation of straight-chain aliphatic derivatives which are then modified to provide appropriate diketogroups, combined with a diol or two halogen atoms, in positions suitable to allow the subsequent cyclyzation into the furanone ring structure to form FURANEOL or its desired homologues (U.S. Pat. No. 3,629,292; Swiss Pat. No. 474,501). Difficulties with these processes, however, are that they involve many expensive operating stages and give rather low yields of the final products.

The object of the present invention is, therefore, to provide a convenient process for the preparation of 2,5-dimethyl-4-hydroxy-3(2H)-furanone and its 2,5-dialkyl homologues.

The present invention is based on the use of 2,5-dimethyl-dihydro-3(2H)-furanone:

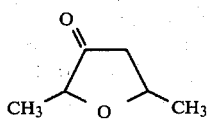

(C.A. 43, 1949, 5424i; C.A. 47, 1953, 7478c; C.A. 57, 1962, 16526d; C.A. 87, P 117769v; German Pat. No. 2,600,864) as a starting compound for the synthesis of FURANEOL. If the above starting compound could be oxidised, the corresponding diketo-derivative might be obtained and then converted to the enol form, i.e. FURANEOL, according to the general scheme;

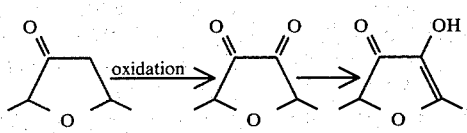

However, FURANEOL has characteristics typical of reducing agents, that is, it has a considerable tendency to be oxidised (B. Wilhalm et al, Chemistry & Industry (1965) 1629) and the choice of a suitable oxidizing agent for a direct reaction of the above type has been very difficult because of the difficulty in stopping the reaction at the desired stage and avoiding the formation of secondary products by further oxidation or degradation. A rather longer, but more controllable route, has therefore been developed.

SUMMARY OF THE INVENTION

Accordingly, the present invention provides a process comprising the steps of:

effecting an aldol condensation reaction between a 2,5-dialkyl-dihydro-3(2H)-furanone having the formula:

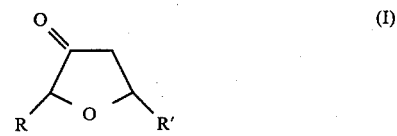

wherein R and R' are each selected from the lower alkyl groups having from 1-3 carbon atoms, and an aldehyde having the formula R"CHO, wherein R" is chosen from the alkyl and isoalkyl groups having from 1 to 6 carbon atoms and aryl groups, under basic aldol condensation conditions at a temperature of from −10° C. to 100° C. to obtain the corresponding aldol compound;

dehydrating the aldol obtained to form the corresponding exocyclic alkene having the formula:

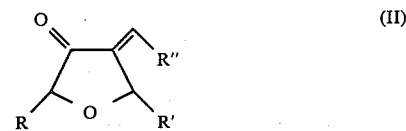

wherein R, R' and R" are as indicated above;

treating the exocyclic alkene (II) with ozone in the presence of one or more participating solvent selected from the group consisting of aliphatic alcohols and acyl compounds having from 1 to 4 carbon atoms (e.g. acetic acid), water, acetone and mixtures thereof, at a temperature from −70° C. to 30° C. to obtain the corresponding hydroperoxy-hemiacetal;

reducing said hydroperoxy-hemiacetal to the corresponding hemiacetal;

converting said hemiacetal to its corresponding 2,5-dialkyl-4-hydroxy-3(2H)-furanone having the formula:

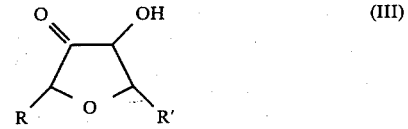

wherein R and R' are as indicated above, by refluxing under acidic conditions in an inert atmosphere; and recovering the product (III).

In the aldol condensation reaction, the aliphatic aldehydes may advantageously be chosen from acetaldehyde and 2-methyl propanal. Aldehydes in which the R" substituent is aryl, such as a phenyl or tolyl group, are also suitable. Benzaldehyde is generally preferred for the purpose. If a substantially quantitative yield of the aldol compound is to be achieved, from 1 to 2 equivalents of the aldehyde, and preferably 1.5 equivalents for every equivalent of furanone should be used in the reaction.

The aldol condensation reaction is carried out under basic conditions, in the presence of either an inorganic base, or an organic base. In the first case, an alkali or alkaline earth metal hydroxide or carbonate, such as sodium hydroxide or potassium hydroxide in aqueous or alcoholic solution, or calcium hydroxide, barium hydroxide, sodium carbonate or potassium carbonate, may be used. In the second base, strong organic bases such as piperidine are preferred. Extremely good results, under economically advantageous conditions, may be obtained by using a catalytic quantity of sodium hydroxide or potassium hydroxide in aqueous solution.

The temperature of the condensation reaction is preferably from 0° C. to 15° C., both to obtain the best results and to avoid polymerisation and other secondary reactions. The reaction time is generally dependent on the temperature; within the range 0° C. to 15° C. indicated above, reaction times of from about ½ an hour to about 2 hours may be used.

The crude aldol recovered from the reaction mass of the first reaction step may be purified by distillation, but this is not strictly necessary. The dehydration of the aldol, may be carried out with either the crude or distilled product to form the corresponding alkene (II) usually with the aid of a catalytic quantity of mineral acid or acid salt, although sometimes it is preferable to use an organic acid, such as p-toluenesulphonic acid. The dehydrating conditions may be varied according to the type of aldehyde R"CHO used in the condensation, all these factors determining the choice of dehydrating agent, for example whether a relatively weak acid salt such as $NaHSO_4$ or $KHSO_4$ or whether p-toluenesulphonic acid is used. The quantity of dehydrating agent used is generally less than 0.01 equivalent. The reaction is carried out at elevated temperatures, generally from 100° to 200° C.; preferably 110° to 160° C. The dehydration may be carried out in separate batches or by a continuous process carried out at low pressure such that the alkene (II) is continuously removed by distillation at it is formed. This latter method of operation, with a moderate vacuum, is preferred as it allows the migration of the exocyclic double bonds to the inside of the furanone ring, between the 4 and 5 positions, to be avoided; such migration would render the subsequent formation of FURANEOL by ozonization impossible. With the conditions mentioned above it is possible to obtain yields of more than 80%, with a selectivity of the order of 90% or more towards the formation of the exocyclic double bond.

A particular aspect of the invention resides in the subsequent oxidation of the alkene (II) to FURANEOL or its 2,5-dialkyl homologues by ozonolysis in the presence of a participating solvent of the formula R'''OH, wherein R''' is hydrogen, a lower alkyl radical with 1–4 carbon atoms (such as methyl, ethyl and propyl) or a $C_1$–$C_4$ acyl radical (such as $CH_3$—CO— or $CH_3 CH_2$ CO—). Thus, the solvent may be chosen for example from methanol, ethanol, acetic acid, water or water/acetone mixtures, but methanol is generally preferred both because it gives very good results and for economic reasons. The ozonization may be carried out within a wide range of temperatures, from about −70° C. to about 25° C.; the −30° C. to 0° C. range is preferred both for reasons of yield and to avoid loss by evaporation.

In practice, the ozone may be fed to the reaction medium in a current of air or oxygen. A peculiarity of this stage of the process of the invention is that the participating solvent reacts with the ozonide according to the reaction:

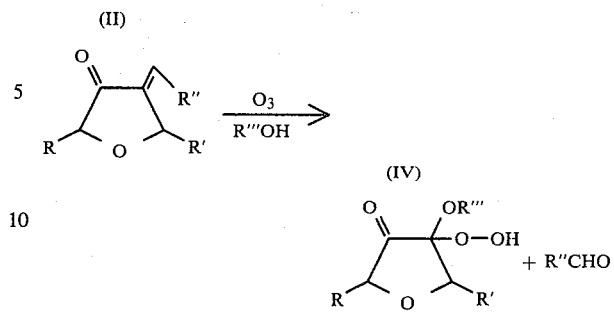

forming a hydroperoxyacetal (IV) which is stable, whereby the oxidation does not proceed any further. The compound (IV) may easily be reduced to the corresponding hemiacetal (V) and then converted to the final product (III) by the reaction:

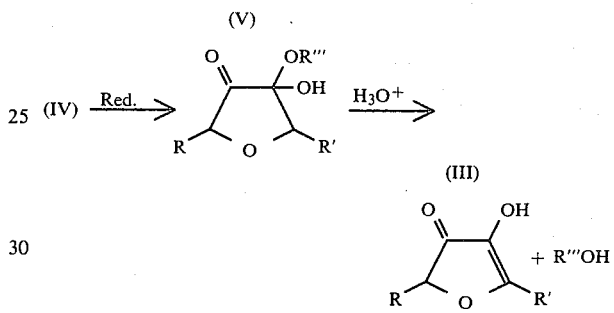

The reduction of the hydroperoxyacetal may be carried out with the aid of a reducing agent such as sulphur dioxide or its salts, or by catalytic hydrogenation. Useful reducing salts are sulphites such as sodium bisulphite and sodium sulphite but thiosulphates may also be used in the presence of potassium iodide, or powdered metallic zinc. Catalytic hydrogenation may be carried out by using Raney nickel, palladium or platinum as the catalyst. Sodium bisulphite is, however, preferred since it is readily available and of low cost. The reaction temperature may vary from 0° C. to 100° C. but the most suitable range is from 10° to 50° C.

For the final conversion of the hemiacetal (V) to the desired FURANEOL or its homologues, various acids may be used, preferably in aqueous solutions such as 0.5 N hydrochloric acid or 10% oxalic acid. Advantageously, the acid is added to the solution obtained by the reduction mentioned above and the resulting mixture is heated under reflux in an inert atmosphere. For example a very good conversion to the final product III may be obtained by adding from 1 to 10 parts by weight of 0.5 N hydrochloric acid for every part by weight of hemiacetal and refluxing the mixture at 80° to 100° C. in an atmosphere of nitrogen for 2 to 6 hours, typically from 3 to 5 hours.

The final product may then be recovered by neutralising the solution, concentrating it, salting it and extracting the product with a suitable solvent (for example dichloromethane or ether), operating either continuously or in separate batches. The crude FURANEOL obtained is semi-crystalline and may be used as it is or may be distilled at reduced pressure to give crystalline FURANEOL (melting point 78° to 79° C.).

The invention will now be further illustrated by the following examples, which are given purely by way of non-limitative example. In the examples, the parts are given by weight unless expressly indicated otherwise.

DESCRIPTION OF THE PREFERRED EMBODIMENTS

Example 1

Part 1: 2,5-dimethyl-4-ethylidene-dihydro-3(2H)-furanone.

20 parts by weight of 2,5-dimethyl-dihydro-3(2H)-furanone, and 56 parts by weight of 28% aqueous acetaldehyde are placed in a flask provided with an agitator, a thermometer and an ice/water bath. An aqueous 20% solution of potassium hydroxide is added drop by drop at 5° C. until the solution is clearly alkaline (pH greater than 12). The reaction mixture is agitated for a further hour at 0° to 10° C. It is then acidified with a few drops of 10% hydrochloric acid and the clear solution is salified with 5 to 8 grams of sodium chloride. The oil phase is extracted with three 30 ml portions of dichloromethane. After evaporation of the unreacted acetaldehyde and the solvent, about 28 grams of aldol residue ($n_D^{20} = 1.4620$) are obtained consisting of a mixture of at least five aldol isomers (which can be distilled at 1.5 mm Hg and at 80° to 92° C. to give a purified aldol, with $n_D^{20} = 1.4590$).

The crude aldol obtained (28 g) is mixed with 0.2 grams of p-toluenesulphonic acid and placed in a Claisen flask, this latter being provided with a first thermometer immersed in the reaction mass and a second thermometer for measuring the temperature of the vapour. The flask is connected, through a small condenser and a collecting flask, with a water-suction pump, regulated so as to produce a vacuum of about 100 to 130 mm Hg. The reaction mixture is heated slowly and the dehydration starts at about 110° to 130° C.; the alkene (II) starts to distil over at between 130° and 150° C. (temperature of the mass). Within about 15 minutes a total of about 24 grams of oil ($n_D^{20} = 1.4560$), together with water, are collected. About 80% of the oil consists of two alkene isomers while about 20% of it consists of unreacted aldol. A 12 inch, Goodloe rectifying column is used to distil the 2,5-dimethyl-4-ethylidene-dihydro-3(2H)-furanone which distils over at 70° to 90° C. at 20 mm Hg. The product, consisting of a mixture of two isomeric forms in a 3:1 ratio, has an $n_D^{20}$ value of 1.4620 to 1.4670 and a content of less than 5% by weight of the endocyclic isomer. About 70% of the alkenes are recovered. The aldol residue is recycled.

Part 2: —FURANEOL 10 grams of 2,5-dimethyl-4-ethylidene-dihydro-3(2H)-furanone obtained by the method of Part 1 are reacted with ozone at −15° C. in 40 ml of methanol, using an oxygen/ozone current containing 4% of ozone, fed in by means of a tube having a porous septum of sintered glass at its end immersed in the reaction mixture. When, from a sample of the reaction mixture (analysed by means of chromatography in the vapour phase on FFAP 15% in a 2 m column at 180° C.) it is found that all the alkene (II) has reacted, the reaction mixture is mixed with 45 ml of water and reduced portion wise with 4 grams of sodium bisulphite, under agitation at 10° to 15° C., until tests with potassium iodide paper are negative. A further 0.5 grams of sodium bisulphite are then added and the reaction mixture is concentrated under a pressure of 30 to 50 mm Hg until the greater part of the methanol has been removed. The residue (about 20 ml) is then heated under reflux in an atmosphere of nitrogen for 4 hours. After cooling and neutralising to about pH=6, the reaction mixture is saturated with sodium sulphate and extracted continuously with dichloromethane for 2 hours. After the evaporation of the solvent from the extract, about 7 grams of residue having a strong odour of burnt sugar are obtained. This residue becomes semi-crystalline after being left overnight. 4 to 4.5 grams of white crystalline FURANEOL are obtained by means of distillation at 0.5 mm Hg at 80° to 90° C. From the NMR analysis (nuclear magnetic resonance) it is found that the product has a typical quadruplet at 4.5 $\tau$ (a proton adjacent the methyl next to the furan ring oxygen), a singlet of methyl at 2.36 $\tau$ adjacent to the double bond, and a doublet of methyl at 1.5 $\tau$.

EXAMPLE 2

Part 1: 2,5-dimethyl-4-isobutylidene-dihydro-3(2H)-furanone

Three parts of 2,5-dimethyl-dihydro-3(2H)-furanone and 4.5 parts of 2-methyl-propanal in ten parts of methanol are cooled to 10° C. 0.65 ml of 20% aqueous potassium hydroxide are added over 10 minutes under agitation between 15° and 30° C., and the agitation is continued for a further hour. The reaction mixture is then neutralised with a few drops of acetic acid. After salting and extraction with dichloromethane as in Example 1 (Part 1) a total of about 4.5 g of aldol is obtained (boiling point 80° to 90° C. at 1 mm Hg; $n_D = 1.4540$ to 1.4590). By dehydration with 100 mg of potassium bisulphate at about 150° C. and 30 mm Hg, about 2 g of 2,5-dimethyl-4-isobutylidene-dihydro-3(2H)-furanone are obtained; boiling point at 30 mm Hg: 120° C.; $n_D = 1.4650$. NMR analysis shows the presence of two methylenic protons at 6.15 $\tau$ and at 6.25 $\tau$.

Part 2: FURANEOL

Three grams of the product obtained by the method of Part 1 above are reacted with ozone in 25 ml of ethanol at −10° C. in the manner described in Example 1, Part 2. After the addition of 15 ml of water, the product of the reaction with ozone is reduced with one gram of sodium bisulphite at 25° to 30° C. until negative results are obtained to the test with potassium iodide paper. The reaction mixture is then concentrated at 30 mm Hg until a residual volume of about 15 ml is obtained and is then heated under reflux for 10 hours in an atmosphere of nitrogen; the product is neutralised to pH=6, then saturated with sodium chloride and extracted with four 30 ml portions of dichloromethane. After evaporation, the residue (about 2.2 g) is distilled at 0.5 mm Hg, giving a main fraction of about 1.1 g ($n_D = 1.5100$) which crystallises as FURANEOL.

EXAMPLE 3

Part 1: 2,5-dimethyl-4-benzylidene-dihydro-3(2H)-furanone 10 g of 2,5-dimethyl-dihydro-3(2H)-furanone and 15 g of newly distilled benzaldehyde are mixed together in 45 ml of methanol. The mixture is cooled to 10° to 15° C., 5 g of 33% aqueous sodium hydroxide are added under agitation and the agitation is continued for a further 2 hours at 25° C. The reaction mixture is then acidified with 5 N hydrochloric acid and extracted with three 50 ml portions of ether. The ether extract is washed with a saturated aqueous solution of sodium chloride and, after evaporation of the ether, the residue is distilled in a Vigreux column giving a principle fraction of 8 to 9 grams at 110° to 130° C. under 1 mm Hg;

$n_D$=1.5475 to 1.5530. This fraction consists of an isomeric mixture of 2,5-dimethyl-4-benzylidene-dihydro-3(2H)-furanone (ratio of about 2:1 ascertained by means of chromatography in the vapour phase on DC 550 at 15% in a 2 m column at 230° C.).

Part 2: FURANEOL 4 grams of the product obtained in part 1 above in 20 ml of methanol are reacted with ozone in the manner described in Example 1, part 2. After an addition of 10 ml of water and reduction with 1.5 g of sodium bisulphite, the methanol is evaporated under slight vacuum and the mixture is heated under reflux with 10 ml of 0.5 N hydrochloric acid for about 3 hours in an atmosphere of nitrogen. The residue is neutralised to a pH of about 6, then saturated with sodium chloride and extracted with four 30 ml portions of dichloromethane. After the evaporation, a residue of about 3 grams is obtained from which about 1.3 grams of FURANEOL, having the same characteristics as that of Example 1, is obtained by means of distillation.

EXAMPLE 4 (FURANEOL)

6 grams of 2,5-dimethyl-4-ethylidene-dihydro-3(2H)-furanone obtained according to Example 1, Part 1 are dissolved in a mixture of 25 ml of acetone and 12.5 ml of water and are reacted with ozone at −10° C. in the manner described in Example 1, Part 2. The reaction product is mixed with 12.5 ml of water and reduced at 20° to 30° C. with 2 g of sodium bisulphite. The mixture is evaporated at 30 mm Hg until a residual volume of 16 ml is obtained to which 16 ml of 0.5 N hydrochloric acid are added. The mixture is heated under reflux for 5 hours in an atmosphere of nitrogen. After neutralisation with sodium carbonate to a pH of about 6 and saturation with sodium chloride, the mixture is extracted with four 50 ml portions of dichloromethane. After the evaporation of the solvent and distillation of the residue, 2 grams of a main fraction (boiling point 80° to 90° C. at 0.5 mm Hg) are obtained which crystallises when left in the form of pure FURANEOL.

What is claimed is:

1. A process comprising the steps of:
effecting an aldol condensation reaction between a 2,5-dialkyl-dihydro-3(2H)-furanone having the formula:

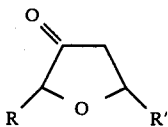

wherein R and R' are each selected from the lower alkyl groups having from 1–3 carbon atoms, and an aldehyde having the formula R"CHO, wherein R" is chosen from alkyl and isoalkyl groups having from 1 to 6 carbon atoms and aryl groups, under basic conditions at a temperature of from −10° C. to 100° C. to obtain the corresponding aldol compound;
dehydrating said aldol compound to form the corresponding exocyclic alkene having the formula:

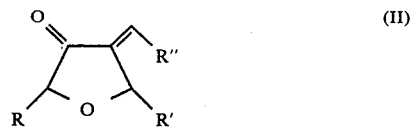

wherein R, R' and R" have the significations indicated above;
treating said exocyclic alkene (II) with ozone in the presence of a participating solvent selected from the group consisting of aliphatic alcohols and acyl compounds having from 1 to 4 carbon atoms, water, acetone and mixtures thereof, at a temperature of from −70° C. to 30° C. to obtain the corresponding hydroperoxyhemiacetal;
reducing said hydroperoxy-hemiacetal to the corresponding hemiacetal;
converting said hemiacetal to its corresponding 2,5-dialkyl-4-hydroxy-3(2H)-furanone having the formula:

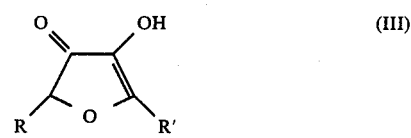

wherein R and R' have the significations indicated above, by refluxing under acidic conditions in an inert atmosphere; and
recovering said 2,5-dialkyl-4-hydroxy-3(2H)-furanone (III).

2. A process as in claim 1, wherein said aryl groups are selected from phenyl and tolyl groups.

3. A process as in claim 1 or 2, wherein said aldol condensation reaction is effected in the presence of an inorganic base selected from the group consisting of hydroxides and carbonates of alkali- and alkaline-earth metals.

4. A process as in claim 1 or 2, wherein said aldol condensation reaction is effected in the presence of an organic base comprising piperidine.

5. A process as in claim 1, wherein said 2,5-dialkyl-dihydro-3(2H)-furanone is 2,5-dimethyl-dihydro-3(2H)-furanone, said aldehyde is acetaldehyde, said participant solvent is methanol, said reducing agent is sodium bisulphite and said aldol condensation reaction is carried out in the presence of an alkali metal hydroxide.

6. A process as in claim 1, wherein said aldehyde is 2-methyl-propanal.

7. A process as in claim 1, wherein said aldehyde is benzaldehyde.

8. A process according to claim 1, wherein said participating solvent is aqueous acetone.

* * * * *